United States Patent [19]

Grant et al.

[11] Patent Number: 4,945,249
[45] Date of Patent: Jul. 31, 1990

[54] REMOTE SENSING SYSTEM

[75] Inventors: Andrew I. Grant, Surrey; Martyn T. MacPherson, Guildford; David G. Stevens, Hampshire, all of England

[73] Assignee: The British Petroleum Company plc, London, England

[21] Appl. No.: 294,087

[22] Filed: Jan. 5, 1989

[30] Foreign Application Priority Data

Jan. 12, 1988 [GB] United Kingdom ............... 8800583

[51] Int. Cl.$^5$ ............................................. G01N 21/64
[52] U.S. Cl. ................................ 250/461.1; 250/253; 364/498
[58] Field of Search ............... 250/253, 461.1; 356/326, 328; 364/498

[56] References Cited

U.S. PATENT DOCUMENTS

| | | | |
|---|---|---|---|
| 4,318,616 | 3/1982 | Chamran et al. | 356/332 |
| 4,517,458 | 5/1985 | Barringer | 250/253 |
| 4,572,667 | 2/1986 | Rodgers | 356/317 |

FOREIGN PATENT DOCUMENTS

| | | |
|---|---|---|
| 0041764 | 12/1981 | European Pat. Off. . |
| 1516281 | 7/1978 | United Kingdom . |
| 2089029 | 6/1982 | United Kingdom . |
| 2112930 | 7/1983 | United Kingdom . |

OTHER PUBLICATIONS

William R. Hemphill, Arnold F. Theisen and R. Michael Tyson, "Laboratory Analysis and Airborne Detection of Materials Stimulated to Luminescence by the Sun", *Journal of Luminescence*, vol. 31/32, Part II (Dec. 1984), pp. 724–726, Copyright © Elsevier Science Publishers B.V.

J. R. Moore, "Measurement of Spectral Power Distribution", *New Developments and Applications in Optical Radiation Measurement (Sira)*, Proc. SPIE, vol. 234, pp. 86–90 (1980).

Primary Examiner—Constantine Hannaher
Attorney, Agent, or Firm—Larry W. Evans; Joseph G. Curatolo

[57] ABSTRACT

Apparatus for detecting an anomaly, (e.g. the presence of a hydrocarbon seep) at or near a water or land surface comprises means for generating a beam, preferably a pulsed beam, of primary light radiation, preferably ultra-violet light, and directing the beam towards the surface. The beam is sufficiently intense and of such a spectral composition that the beam causes the anomaly, if present, to emit secondary light radiation. The apparatus also comprises means for collecting the secondary light radiation, or means for collecting solar induced secondary light radiation, spectral analysis means for analysing the spectrum of the secondary radiation, and a high resolution, multi-element digitizing detector for recovering the analyzed secondary radiation. The detector has a plurality of detection channels positioned across the spectrum of the backscattered primary radiation and emitted secondary radiation, the channels being software configurable and under the control of a digitally addressable computer-operated controller. The concentration of used channels across the plurality of channels is adjustable and increasable in the regions of the spectrum of greatest interest and decreasable in the regions of least interest.

11 Claims, 2 Drawing Sheets

REMOTE SENSING SYSTEM

This invention relates to an airbone optical spectrometer system for detecting anomalies at or near the surface from the air.

The detection of anomalies in optical response at, above or below marine surfaces and at or above land surfaces can be of great value in identifying and locating phenomena due to materials such as pollutants and minerals. Incorporating optical equipment on an airbone platform for this task provides a rapid reconnaissance technique.

Minerals may be exposed by weathering to produce the anomalies or there may be a surface expression of subsurface materials.

A particularly important example of the latter is the natural seepage of hydrocarbons from subterranean reservoirs which may be either on or offshore.

Offshore petroleum exploration technology, especially the use of reflection seismic, has developed to the extent that the structure and thickness of potentially oil-bearing rocks can be determined with a degree of confidence which is limited mostly by cost. However, many areas still have either widely scattered wells or no wells at all, and in such places geochemical information may be insufficient to determine whether petroleum has been generated and its subsequent history.

In such circumstances there is a need for direct information about the occurrence of petroleum in the subsurface. Fortunately, the gas phase of petroleum is buoyant and has the capacity, demonstrated in several mature offshore production provinces, to breach trap seals and rise through the overburden to give flowing gassy seeps in the sea. Bubble plumes caused by gas seepage from oilfields have been reported, for example, from the North Sea, the Gulf of Mexico and offshore Brunei. Some bubbles may contain oil or gas condensate in addition to natural gas and this liquid phase will form a slick on the surfaces. In rough water the oil may become emulsified in the surface layer.

British patent specification No. 1516281 discloses a method for determining the presence of hydrocarbon seeps in the sea comprising (a) traversing an area of the sea in a moving vehicle,
(b) generating a beam of primary light radiation and directing said light beam towards the sea, said beam being of sufficient intensity and of such wavelength composition to produce secondary light radiation in sub-surface zones of the sea, said secondary radiation being located near the surface of the sea,
(c) receiving secondary light radiation emanating from said zones,
(d) determining the intensity of said received secondary light radiation,
(e) observing the positions in said area wherein said secondary light radiation was received, and
(f) repeating the aforesaid steps (a)–(e).

This method involves the use of fixed and pre-determined optical band coverage with fixed and predetermined low spectral resolution in the UV to red wavelength (300–800 nanometers).

We have now devised an improved, high spectral resolution, airbone optical detector system for, but not limited to, the remote detection of radiation from UV to far red wavelengths, whose spectral resolution across the wavelength region is computer configurable and can be adjusted according to the application.

Thus, according to the present invention there is provided apparatus for detecting an anomaly at or near a water or land surface which apparatus comprises means for generating a beam, preferably a pulsed beam, of light radiation, preferably ultra-violet light, and directing the beam towards the surface, the beam being sufficiently intense and of such a spectral composition that the beam causes the anomaly, if present, to emit secondary light radiation, means for collecting the secondary light radiation, or means for collecting solar induced secondary light radiation, and spectral analysis means for analysing the spectrum of the secondary radiation, and a high resolution, multi-element digitising detector for recovering the analysed secondary radiation, having a plurality of channels across the spectrum of the emitted secondary radiation, the channels being software configurable and under the control of a digitally addressable computer-operated controller, the concentration of used channels across the plurality of channels being adjustable and increasable in the regions of the spectrum of greatest interest.

Suitable means for generating the beam of primary light radiation include a laser.

The laser radiation may be provided by a continuous-wave laser with constant intensity. The laser radiation may have an intensity which varies with time, for example modulated or pulsed laser radiation. The laser radiation may be provided by a modulated or chopped, continuous-wave laser. The intensity of the radiation may vary in the form of a sine wave or square wave or may be pulsed. The laser radiation may be provided by a pulsed laser, for example an ultra-violet excimer, a visible metal gas discharge laser, a flash lamp-pumped or a semi-conductor pumped solid-state laser. Such lasers may be Nd-YAG lasers, ruby lasers or pulsed argon ion lasers. The pulsed lasers may have nanosecond or picosecond pulse widths. The picosecond pulsed lasers may comprise a source laser, a synchronously pumped, cavity dumped, dye laser with amplifiers and further wavelength shifting units. The lasers may have regenerative amplification systems with high repetition rate may be included in the picosecond source of laser radiation.

Suitable light collection means include an optical telescope.

Suitable spectral analysis means include a grating spectrograph.

Output from the detector will normally be logged and may be displayed and/or stored as desired.

When the application is for petroleum prospecting, the primary light is preferably generated by an ultra-violet exicmer laser producing light of wavelength 308 nm and the detection system is capable of receiving secondary radiation from petroleum films or emulsions. The spectral region of interest covers the ultra violet light induced fluorescent emission in the wavelength range from 300 to 800 nm. The lower wavelength boundary is determined by the excimer laser operating preferably at 308 nm; this wavelength has been shown to be the most advantageous for excitation of petroleum aromatic components by virtue of their high absorption coefficients at 308 nm and high fluorescence quantum yield.

The detector may contain 512, 1024 or 2048 channels or more but only 90 may be required to provide adequate spectral coverage for the phenomenon of interest. The advantage in using the minimum number of channels to analyse the responses from the chosen phenomenon is that the data rates to be logged, and, therefore, the total signal acquired, can be kept to a minimum.

Specifically for this application the regions of interest are the water Raman signal, shifted 3000-3600 wavenumbers from the wavelength of the primary radiation and the rising edge of the oil fluorescence, whereas the long wavelength fluorescence need only be analysed to low spectral resolution.

Thus, the invention may be flexibly configured to provide high spectral resolution in the spectral regions of interest, i.e., from 300 nm to 500 nm, with much lower spectral resolution beyond. The non-used channels at any moment in time are redundant but when appropriate (for the appraisal of a different phenomenon) may be brought into operation by means of the digitally addressable, software configurable controller.

According to another aspect of the present invention there is provided a method for detecting an anomaly at or near a water or land surface by generating a beam, preferably a pulsed beam, of primary light radiation, preferably ultra-violet light, and directing the beam towards the surface, the beam being sufficiently intense and of such spectral composition that the beam causes the anomaly, if present, to emit secondary light radiation, collecting the secondary light radiation, or collecting solar induced secondary radiation, analysing the spectrum of the secondary radiation and detecting the analysed radiation by means of a high resolution, multi-element digitising detector having a plurality of channels across the spectrum of the emitted secondary radiation, the channels being software configurable and under the control of a digitally addressable computer operated controller, the concentration of used channels across the plurality of channels being adjusted and increased in the region of the spectrum of greatest interest and decreased in the regions of least interest.

The invention is illustrated by but not limited with reference to the accompanying drawings.

Figure 1:
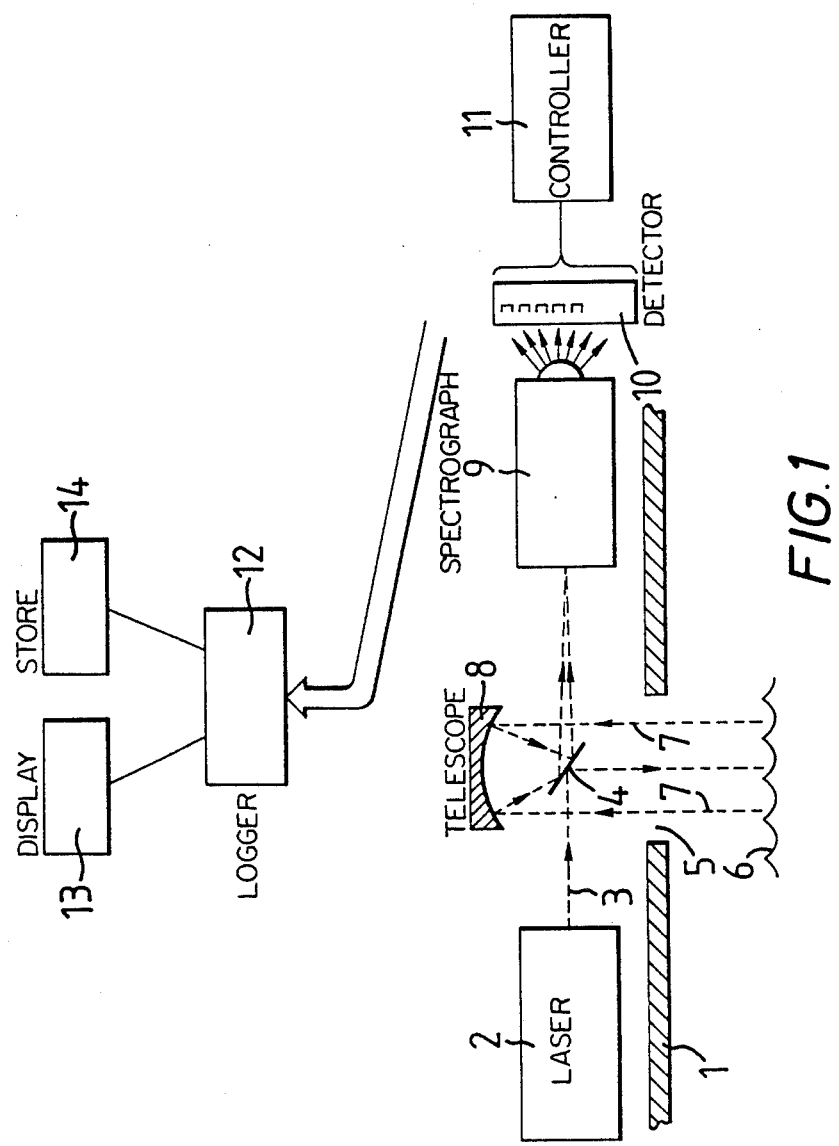
FIG. 1 is a diagrammatic representation of an airbone laser fluorosensing system.

The system is fitted within the interior of a light aircraft 1. It comprises an excimer laser 2 emitting a pulsed beam 3 of primary ultra-violet light radiation which is reflected by a mirror 4 through a port 5 in the underside of the aircraft and directed downwardly to the surface of the sea 6.

Rays of secondary light radiation 7 induced by the primary beam are collected by a reflecting telescope 8, further reflected by the mirror 4 and passed through a grating spectrograph 9 which disperses the light onto a gateable, intensified optical multi-channel detector 10 which is software configurable and capable of multi-element digitising.

Figure 2:
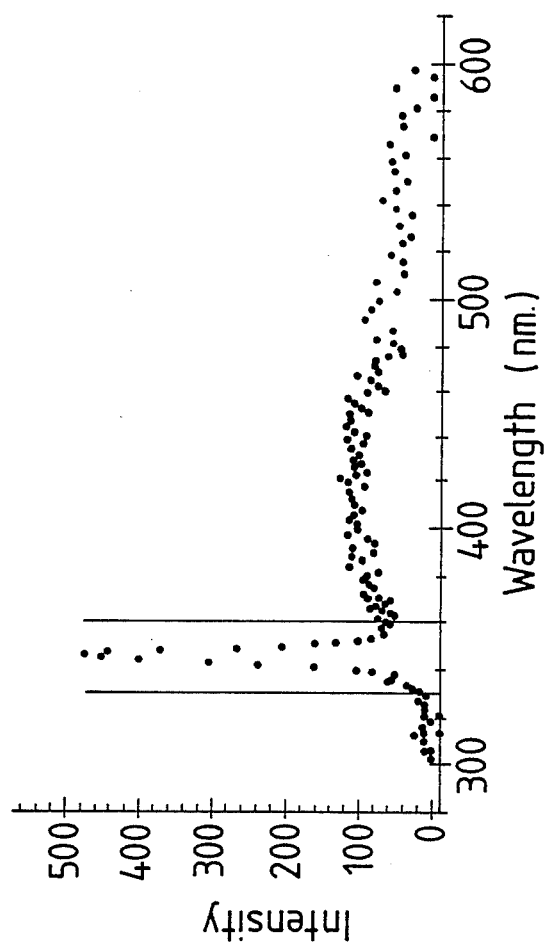
FIG. 2 is a graphical illustration of variable channel digitization.

As an example, the spectral region given 310 nanometers to 360 nanometers may be configured to have a spectral resolution of one channel per nanometer, and the spectral region from 361 nanometers to 500 nanometers may be configured to have a spectral resolution of one channel for every four nanometers and the resolution beyond 500 nanometers may be configured to be one channel for every eight nanometers. The variable channel digitization is illustrated by FIG. 2. The remaining channels are redundant for this particular use, but channels may be brought into and out of use as and when required.

From the detector, signals are passed to a digitally addressable software configurable controller 11 which controls the effective digitisation across multi-element detector.

Data is logged, displayed and stored by logger 12, display unit 13 and store 14.

We claim:

1. Apparatus for detecting an anomaly at or near a water or land surface which apparatus comprises means for generating a beam of primary light radiation, and directing the beam towards the surface, the beam being sufficiently intense and of such a spectral composition that the beam causes the anomaly, if present, to emit secondary light radiation, means for collecting the secondary light radiation, or means for collecting solar induced secondary light radiation, and spectral analysis means for analysing the spectrum of the secondary radiation, and a high resolution, multi-element digitising detector for detecting the analysed radiation, having a plurality of channels across the spectrum of the emitted secondary radiation, the channels being software configurable and under the control of a digitally addressable computer-operated controller, the concentration of used channels across the plurality of channels being adjustable and increasable in the regions of the spectrum of greatest interest and decreasable in the regions of least interest.

2. Apparatus according to claim 1 wherein the means for generating the beam of primary light radiation is a laser.

3. Apparatus according to claim 2 wherein the laser is a pulsed laser.

4. Apparatus according to claim 1 wherein the means for generating the primary light radiation is means for generating ultra-violet light.

5. Apparatus according to claim 4 wherein the means for generating ultra-violet light is an excimer laser.

6. Apparatus according to claim 4 wherein the means for generating a pulsed beam of ultra-violet light is capable of generating light of wavelength 308 nm.

7. Apparatus according to claim 1 wherein the means for collecting the secondary light radiation is an optical telescope.

8. Apparatus according to claim 1 wherein the spectral analysis means is a grating spectograph.

9. Apparatus according to claim 1 wherein the detector is capable of detecting light in the wavelength range of 300 to 800 nm.

10. Apparatus according to claim 9 wherein the apparatus is capable of providing relatively high adjustable spectral resolution in the wavelength region up to 500 nanometers and relatively low spectral resolution for the wavelength beyond 500 nanometers.

11. A method for detecting an anomaly at or near a water or land surface by generating a beam of primary light radiation, and directing the beam towards the surface, the beam being sufficiently intense and of such spectral composition that the beam causes the anomaly, if present, to emit secondary light radiation, or collecting solar induced secondary radiation, analysing the spectrum of the secondary radiation and detecting the analysed radiation by means of a high resolution, multi-element digitising detector having a plurality of channels across the spectrum of the emitted secondary radiation, the channels being software configurable and under the control of a digitally addressable computer operated controller, the concentration of used channels across the plurality of channels being ajusted and increased in the region of the spectrum of greatest interest and decreased in the regions of leasft interest.

* * * * *